United States Patent
Sontag

(10) Patent No.: US 6,783,006 B1
(45) Date of Patent: *Aug. 31, 2004

(54) CONTAINER FOR CHEMICALS

(75) Inventor: Christoph Sontag, Bad Säckingen (DE)

(73) Assignee: Syngenta Investment Corp., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 323 days.

(21) Appl. No.: 08/700,427

(22) PCT Filed: Feb. 13, 1995

(86) PCT No.: PCT/EP95/00515

§ 371 (c)(1),
(2), (4) Date: Aug. 26, 1996

(87) PCT Pub. No.: WO95/23099

PCT Pub. Date: Aug. 31, 1995

(30) Foreign Application Priority Data

Feb. 24, 1994 (CH) ................................. 542/94

(51) Int. Cl.⁷ ............................................. B65D 85/84
(52) U.S. Cl. ................................................... 206/524.1
(58) Field of Search ............................... 206/484, 524.7

(56) References Cited

U.S. PATENT DOCUMENTS

| | | | | |
|---|---|---|---|---|
| 3,198,740 A | | 8/1965 | Dunlop, Jr. | |
| 3,695,989 A | * | 10/1972 | Albert ................. | 206/524.7 X |
| 3,892,905 A | * | 7/1975 | Albert ................. | 206/524.7 X |
| 4,481,326 A | | 11/1984 | Sonenstein | |
| 5,080,226 A | * | 1/1992 | Hodakowski et al. ................... | 206/524.7 X |
| 5,183,492 A | | 2/1993 | Suchy et al. | |
| 5,209,771 A | | 5/1993 | Meyer | |
| 5,222,595 A | | 6/1993 | Gouge et al. | |
| 5,224,601 A | * | 7/1993 | Gouge et al. ............ | 206/524.7 |
| 5,248,038 A | * | 9/1993 | Hodakowski et al. ..... | 206/524.7 |
| 5,253,759 A | * | 10/1993 | Gouge et al. ............ | 206/524.7 |
| 5,279,421 A | * | 1/1994 | Gouge et al. ............ | 206/484 |
| 5,280,835 A | * | 1/1994 | Edwards et al. .......... | 206/484 |
| 5,310,563 A | * | 5/1994 | Curtis et al. ............ | 424/616 |
| 5,323,906 A | * | 6/1994 | Gouge et al. ............ | 206/524.7 |
| 5,328,025 A | * | 7/1994 | Hodakowski et al. ..... | 206/524.7 X |
| 5,330,047 A | * | 7/1994 | Gouge et al. ............ | 205/524.7 X |
| 5,341,932 A | * | 8/1994 | Chen et al. ............. | 206/524.7 |
| 5,346,068 A | * | 9/1994 | Gouge et al. ............ | 206/524.7 |
| 5,351,831 A | * | 10/1994 | Gouge et al. ............ | 206/524.7 |
| 5,358,103 A | * | 10/1994 | Hodakowski et al. ..... | 206/524.7 X |
| 5,394,990 A | * | 3/1995 | Edwards et al. .......... | 206/524.7 |
| 5,429,242 A | * | 7/1995 | Edwards et al. .......... | 206/484 |
| 5,558,228 A | * | 9/1996 | Jackisch et al. ......... | 206/524.7 |
| 5,624,034 A | * | 4/1997 | Edwards et al. .......... | 206/484 |
| 5,691,015 A | * | 11/1997 | Tsukamoto et al. ....... | 206/524.7 |
| 5,827,586 A | * | 10/1998 | Yamashita et al. ....... | 206/524.7 |

FOREIGN PATENT DOCUMENTS

| | | |
|---|---|---|
| DE | 4113786 | 11/1991 |
| EP | 0132726 | 2/1985 |
| EP | 0518689 | 12/1992 |
| GB | 0776893 | 6/1957 |
| GB | 1583082 | 1/1981 |
| GB | 2244258 | 11/1991 |
| WO | 9308095 | 4/1993 |

OTHER PUBLICATIONS

Derwent Abstract 85–032599 of EP 132726 (1985).

* cited by examiner

*Primary Examiner*—Deant Nguyen
*Assistant Examiner*—Michael J. Fisher
(74) *Attorney, Agent, or Firm*—Thomas Hamilton

(57) ABSTRACT

The present invention relates to sealed containers for storing chemicals, the wall of said containers comprising at least two superimposed single layer homogeneous and water-soluble polymer films that stick together by weak adhesion and are separable without tearing the films. The present invention also relates to the fabrication of such sealed containers and to their use for the preparation of aqueous application formulations.

13 Claims, No Drawings

CONTAINER FOR CHEMICALS

The present invention relates to sealed, water-soluble containers made of polymer films for preserving chemicals, and to the use thereof for the preparation of formulations for different fields of use, especially for formulations for the application of agrochemicals.

BACKGROUND OF THE INVENTION

Water-soluble containers made of polymer films into which chemicals are filled and which permit the application of chemicals, while avoiding contact therewith, are known. However, polymer films that are commonly used for such containers exhibit failings, typically air pockets, small pores or entrapped dust and other particles. In addition, these polymer films tend to become brittle at low temperature or as a result of the plasticisers present in the film leaching out. Containers made of such polymer films are, therefore, susceptible to damage resulting from mechanical stress during storage and on handling and application. Furthermore, the chemicals in the container can leak through pores or fine cracks in the film and contaminate the environment.

To counteract these problems, it has already been proposed to use a laminated film for fabricating such containers, i.e. a polymer film obtained by pressing together two or more originally separate layers by pressure, heat, crosslinking, fusing or bonding. In these laminated films consisting of a plurality of sheets integrally joined together the occurrence of permanent pores is statistically very insignificant and the strength of the film is enhanced by the layers joined together. A container which is fabricated by using such films is disclosed, inter alia, in DE-OS-41 13 786.

It is, however, very much more troublesome to make laminated films than single layer films, as they are obtained in a second process step from prefabricated monofilms by pressure, heat, crosslinking, fusing or bonding. Laminating requires either additional adhesives or energy in the form of pressure or heat. The fabrication of laminated films is therefore far more cost-intensive than that of monofilms.

SUMMARY OF THE INVENTION

It is therefore the object of this invention to provide sealed, water-soluble containers of superior strength and impermeability which are inexpensive and technically simple to manufacture.

DETAILED DESCRIPTION OF THE INVENTION

It has been found that this object can be achieved by using for the wall of the container at least two single-layer superimposed polymer films. Surprisingly, it has been found that not only is the leakage of liquid from containers having walls made of such single films through the small pores present in each of the single films prevented, but that said containers are in addition extremely resistant to mechanical stresses even at low temperatures and have tear strength properties that are very markedly superior to those of equally thick monofilms and even greatly surpass those of laminated films.

Accordingly, the invention postulates the use of sealed containers for preserving chemicals, the wall of which containers is formed from at least two superimposed single-layered homogeneous and water-soluble polymer films.

The chemicals may be inorganic or organic compounds which are typically formulated as aqueous solutions, gels, powders, emulsions, suspensions or dispersions. The chemicals in the container are preferably dissolved or dispersed in a liquid or a gel, or they are in the form of water-dispersible powders or granulates.

The chemicals can contain minor amounts of water, conveniently up to 5% by weight, preferably up to 2% by weight, based on the amount of the contents of the water-soluble container. It is also possible, however, for the chemicals to be in the form of aqueous concentrates if they contain additives that prevent the dissolution of the water-soluble containers. Such additives are typically electrolytes. These concentrates may contain up to 50% by weight, more preferably from 10 to 40% by weight, of water (q.v. for example EP-A1-0 518 689).

The content of chemicals may be 100% by volume, based on the volume of the water-soluble container. It may be advantageous, however, to choose a content in the range from 40 to 100% by volume in order to influence the structural integrity of the container with a specific volume of gas, e.g. air or nitrogen, such that, when preparing aqueous spray mixtures, the contents do not deposit on the bottom of the mixing tank upon dissolution of the water-soluble container and would at least hinder dissolution. Besides air and nitrogen it is also possible to use other gases to produce a defined atmosphere, for example rare gases or carbon dioxide.

The water-soluble wall of the containers preferably consists of natural unmodified or modified polymers or synthetic polymers. The polymers are desirably so chosen that they have a sufficient mechanical stability and do not burst during transportation or if accidentally dropped. The polymer films used for the container wall may be identical or different. The use of at least two monofilms permits the useful combination of films with different properties, for example the combination of an inner film having good chemical compatibility with an outer film which has a high rate of dissolution.

The container of this invention preferably has a wall comprising two or three water-soluble polymer films. The overall thickness of the container wall is typically 20 to 200 $\mu$m, preferably 30 to 100 $\mu$m. The container has a capacity of 5 ml to 10 000 ml, more particularly of 10 to 2000 ml.

The chosen wall thickness will depend, inter alia, on the make-up of the package system. Containers in the form of heat-sealed bags are usually thin-walled, whereas erect or free-standing systems are thicker walled. The type of seal can also affect the wall thickness. The container may also be of mono or biaxially drawn plastic films.

Suitable water-soluble polymers are inert to the chemicals employed, for example organic solvents, surfactants, active compounds and other adjuvants. They may typically include homo- or copolymeric polyalkylene ethers, for example polyethylene glycols or copolyethylene propylene glycols, starch and modified starch, modified celluloses such as partially alkylated and partially acylated celluloses or hydroxyalkylated or carboxyalkylated celluloses (hydroxymethylcellulose, hydroxyethylcellulose, hydroxypropylcellulose, carboxymethylcellulose), polyvinyl ethers such as polymethyl vinyl ether, polymethoxyethyl vinyl ether, polyhydroxyethyl vinyl ether, polyhydroxypropyl vinyl ether and polycarboxymethyl vinyl ether, polysulfonic acids, polysulfates and polycarboxylic acids and the hydroxyalkyl esters and salts thereof, for example polyvinylsulfonic acids or polyvinylsulfates, polystyrenesulfonic acids or sulfated polyphenols, polyacrylic and polymethacrylic acids, polymaleic acids and the hydroxyethyl esters and salts thereof, sulfonic acid group containing condensates of aldehydes, in particular formaldehyde, and naphthalene, benzene, naphthols, phenols and the salts thereof, low molecular condensates of melamine and/or urea with aldehydes, preferably formaldehyde, polyvinyl pyrrolidones, and polyvinyl alcohol. Particularly suitable copolymers typically include those of at least two monomers selected from the group consisting of vinyl alcohol, vinyl acetate, vinyl ethers, hydroxyalkyl vinyl ethers, acrylic acid, methacrylic acid, maleic acid, maleic acid, hydroxyalkyl acrylates and methacrylates, vinyl pyrrolidone and styrenesulfonic acid. Preferred water-soluble polymers are those containing 50 to 100 mol % of vinyl alcohol units and 50 to 0 mol % of one or more than one comonomer selected from the group consisting of vinyl ether, vinyl acetate, hydroxyalkyl vinyl ether, acrylic acid, methacrylic acid, maleic acid, hydroxyalkyl maleates, acrylates and methacrylates, vinyl pyrrolidone and styrenesulfonic acid. The polymeric wall material is preferably soluble in cold water. To obtain desired mechanical properties, plasticisers may be added to the polymers. In addition, the walls of the containers may also consist of water-soluble polymer mixtures, including polymers mentioned above.

Most preferably, the container wall consists of polyvinyl alcohol films obtainable by hydrolysis of polyvinyl ethers or esters. The degree of hydrolysis may be from 80 to 98%, preferably from 86 to 95%.

The chemicals may be packaged individually or in combination with at least one further chemical, mainly depending on the desired application forms and the properties or the compatibility of said chemicals. The novel container is particularly suitable for the preparation of aqueous use formulations, typically for electrolysis baths, cleansing baths, dye baths, baths for treating or finishing surfaces, hydraulic fluids, baths for leather or textile treatment or finishing, enamelling baths and, in particular, for pesticidal formulations for application as spray mixtures for the treatment and protection of plants, seeds or animals, or animal baths for controlling parasites. The novel container can also contain chemicals which are used for treating water in industry, swimming baths or in the home, as well as chemicals for photographic baths.

Further obects of this invention are the use of the novel container for the preparation of aqueous application formulations, and a process for the preparation of aqueous application formulations, while avoiding contact with the chemicals employed and observing stipulated dosage rates, by putting one or more said novel containers, with stirring, into a mixing tank.

One or more novel containers can be provided with an outer wrapping. This package system constitutes another object of the invention. The outer wrapping may consist of different materials, for example plastics, metals and laminates such as paper/plastic, paper/metal, metal/plastic or paper/plastic/metal. The outer wrapping is not contaminated with chemicals and can therefore be readily reused, disposed of or recycled.

Suitable forms of container for the outer wrapping are typically containers of cardboard, plastic or metal with one or more compartments; collapsible cardboard cartons without or with inner liner that can be made into a multicompartment system; bags and, in particular, erect bags, having one or more compartments which may be designed as partitions; injection moulded, deep-drawn and compression-moulded packages made of plastic materials and having one or more compartments. The packages can be sealed with covers or with diaphragm seals. The outer wrapping is conveniently sealed airtight to ensure adequate storage stability.

Without implying any restriction to this recitation of the subject matter of the invention, the following organic chemicals in the field of agrochemicals can be filled preferably alone or in combination as mixture or formulation into the novel water-soluble containers in the practice of this invention:

A) Solid or liquid agrochemical agents such as pesticides (fungicides, insecticides, herbicides, bactericides), including microorganisms and cell cultures of natural or modified bacteria or fungi;
B) anionic, cationic and nonionic surfactants;
C) organic solvents and vegetable oils;
D) formulation assistants such as thickeners, antifoams, carriers and extenders (fillers);
E) stabilisers and antifeeze agents;
F) protectors for the packaging material (e.g. plasticisers);
G) nutrients for microorganisms or cell cultures;
H) drying agents;
I) safeners;
J) oxygen scavengers.

Most preferably the chemicals are herbicides, insecticides or fungicides and formulation assistants.

By way of illustration, the following agrochemical compounds are suitable for application in the novel container:

fungicides of the classes of the acyl alanines including metalaxyl, furalaxyl, ofurace, benalaxyl and oxalaxyl; of the triazoles including propiconazol, penconazol, difenoconazol, tebuconazol, triadimenol, epoxiconazol, cyproconazol, fenbuconazol, flutriafol, flusilazol and hexaconazol; of the morpholines including denpropimorph, fenpropidin, tridemorph and dimethomorph; of the phenylpyrroles such as fenpiclonil and fludioxonil; and of the aminopyridmidines such as cyprodinil and pyrimethanil. It is also possible to use mixtures of different compounds. Co-components are typically the compounds captan, folpet, thiran, maneb, mancozeb and zineb.

Herbicides of the classes of the phenoxypropionates such as propaquizafop and clodinafop-propargyl, sulfonylureas such as triasulfuron, thifensulfuron, primisulfuron, cinosulfuron, prosulfuron, as well as the compounds described in U.S. Pat. No. 5,209,771; of the chloracetanilides, e.g. metolachlor; of the urea derivatives such as chlortoluron and isoproturon; of the imidazolinones such as imazapyr; of the uracils described in U.S. Pat. No. 5,183,492; or of the cyclohexanediones such as sethoxydim. Mixtures of different compounds can also be used, for example to potentiate the activity or to protect cultivated plants, but not the weeds, from the action of the herbicide. Suitable co-components are typically oxime ether safeners, e.g. oxabetrinil, or quinoline safeners, e.g. cloquintocetmexyl.

Insecticides or acaricides from the classes of the acylureas, e.g. diflubenzuron, hexaflumuron or lufenuron, of the *bacillus thuringiensis* preparations; of the carbamates such as aldicarb, carbofuran, fenoxycarb, furathiocarb or methomyl; of the chlorinated hydrocarbons such as chlordane or endosulfan; of the formamidines e.g. formetanate; of the nitroenamines and derivatives, e.g. imidacloprid; of the organophosphorus compounds including chlorpyrifos, diazinon, monocrotophos, profenofos or terbufos; of the pyrethroids such as cyhalothrin, cypermethrin, deltamethrin or permethrin; and thioureas and derivatives such as diafenthiuron.

The novel containers can also be so designed that a pair of two containers or, as may be required, also a plurality of single containers, are joined together by a water-soluble seal. These container combinations make it possible to use e.g. combinations of active substances such as synergistic mixtures, or combinations of compounds such as mixtures of insecticides or herbicides, that would otherwise suffer loss of activity through direct contact with each other or with formulation assistants and through chemical or physical changes. Problems of too low storage stability can thus be obviated. Furthermore, it is possible in the practice of this invention to package individual components of a total formulation and to enable the end user to prepare the formulation just shortly before use. It is, however, also possible to package different preformulated concentrates individually and to mix them only just before use.

Listed hereinbelow are a number of possibilities for novel container formulations:

a) At least two mutually incompatible different agrochemical agents in at least two integrally joined water-soluble containers. The agrochemical agents may be solid, liquid or dissolved in organic solvents or applied to solid carriers.

b) At least two different emulsifiable concentrates with different agrochemical agents in at least two integrally joined water-soluble containers.

c) At least two different oil-based suspension concentrates with different agrochemical agents in at least two integrally joined water-soluble containers.

d) At least two different different water-dispersible powders with different agrochemical agents in at least two integrally joined water-soluble containers.

e) At least two different different water-dispersible granulates with different agrochemical agents in at least two integrally joined water-soluble containers.

f) At least one emulsifiable concentrate and at least one oil-based suspension concentrate with different agrochemical agents in at least two integrally joined water-soluble containers.

g) At least one emulsifiable concentrate and at least one water-dispersible powder with different agrochemical agents in at least two integrally joined water-soluble containers.

h) At least one emulsifiable concentrate and at least one water-dispersible granulate with different agrochemical agents in at least two integrally joined water-soluble containers.

i) At least one oil-based suspension concentrate and at least one water-dispersible powder with different agrochemical agents in at least two integrally joined water-soluble containers.

j) At least one oil-based suspension concentrate and at least one water-dispersible granulate with different agrochemical agents in at least two integrally joined water-soluble containers.

k) An oil-based suspension concentrate, an emulsifiable concentrate and a water-dispersible powder each with different agrochemical agents in three integrally joined water-soluble containers.

l) An oil-based suspension concentrate, an emulsifiable concentrate and a water-dispersible granulate each with different agrochemical agents in three integrally joined water-soluble containers.

m) An oil-based suspension concentrate or an emulsifiable concentrate, a water-dispersible granulate and a water-dispersible powder each with different agrochemical agents in three integrally joined water-soluble containers.

n) An oil-based suspension concentrate, an emulsifiable concentrate, a water-dispersible granulate and/or a water-dispersible powder with one agrochemical agent, and a different active substance which may or may not be dissolved in an organic solvent in at least two integrally joined water-soluble containers.

o) At least one agrochemical agent and at least one oil-based suspension concentrate, an emulsifiable concentrate, a water-dispersible granulate and/or a water-dispersible powder in at least two integrally joined water-soluble containers.

p) At least one agrochemical agent and a surfactant that optionally contains further formulation assistants in at least two integrally joined water-soluble containers. The formulation assistants may also be present separately in a further water-soluble container.

q) At least one agrochemical agent, an organic solvent and a surfactant that optionally contains further formulation assistants in at least three integrally joined water-soluble containers. The formulation assistants may also be present separately in a further water-soluble container.

r) At least one agrochemical agent and an organic solvent in at least two integrally joined water-soluble containers.

s) At least one microorganism or at least one cell culture as agrochemical agent together with a nutrient medium and at least one surfactant that optionally contains further formulation assistants, in at least two integrally joined water-soluble containers. The formulation assistants or the nutrient medium may also be present separately in a further water-soluble container.

The following specific systems are cited as illustrative examples:

1. (3-methyl-5-cyclopropylpyrimidin-1-yl)phenylamine and 1-(2',4'-dichlorophenyl)-1-(1',2',4'-triazol-1'-ylmethyl)-3-propyl-tetrahydrofuran (insufficient compatibility);

2. 1-[(4'-chlorophenoxy)-2'-chlorophen-1-yl]-1-(1',2',4'-triazol-1'-ylmethyl)-3-methyltetra-hydrofuran and anionic surfactants (crystalline growth of the active compound in the surfactant);

3. standard herbicide of the group of the ureas (Isoproturon®, Chlortoluron®) and triazines (Terbutryn®) and sulfonylureas, for example in the mixture ratios of 100 to 50 to 1 (hydrolysis of sulfonylureas);

4. microorganisms, for example *Bacillus thuringiensis* (strain GC-91) and nutrient (instability of microorganisms with nutrients);
5. solid formulations, for example water-dispersible granulates with antifoams (insufficient compatibility).

The chemicals employed can have a solid, mobile, viscous or gel-like consistency. For reasons of transportability, a solid, viscous or gel-like consistency is preferred. The viscosity of the liquids and gels is preferably from 1000 to 20 000 centipoise, measured by the Brookfield method at 25° C.

The films can be made by per se known methods such as extrusion of a melt or by casting an aqueous solution. This invention permits the combination of films made by different methods and of different composition, so that the wall of the novel containers can be adapted in simple manner to the respective end use.

In addition to their simple and inexpensive manufacture, the novel containers have the advantage that the individually superimposed films form a stronger barrier to the diffusion of product components than a laminated film. Furthermore, the diffusion into the formulation of the plasticisers present in the outermost wrapping is also hindered, so that flexibility and low temperature resistance of the containers are retained longer.

The novel containers are fabricated in per se known manner. Typically, a heat-sealed bag can be made by feeding at least two webs of water-soluble material having a width of 100–300 mm and a thickness of 10–40 µm continuously to a commercial filling machine in which the webs are first welded with a main seam to a bag that is sealed at its end by a transverse weld. The bag so obtained is sealed by a dividing seam after being filled with the desired amount of pesticide concentrate, so as to give on the one hand, a ready-for-use bag containing the pesticide concentrate and, on the other, a new bag prefabricated from the tubular film into which the next portion of active ingredient concentrate can be filled. The welds can be produced thermally at a temperature of c. 180° C., by bonding the seams by prior wetting and subsequent compression as well as by impulse sealing or by high-frequency sealing. In a preferred embodiment of the novel heat-sealed bag, the welds are produced by prior wetting and subsequent compression.

Commercial heat-sealed bag machines suitable for the production of single wall bags may be used for the fabrication of the novel heat-sealed bag. These machines can be adapted in simple manner either by mounting an additional clamp for at least one additional roll of film or by fitting a synchronously driven film transport unit. In the first variant it is essential that the rolls of film have the same diameter to effect uniform transportation. A process for the fabrication of containers by producing a container from polymer films by per se known methods using at least two superimposed single-layered homogeneous and water-soluble polymer films consistutes a further object of this invention.

WORKING EXAMPLES

Example W1

A melalaxyl wettable powder is prepared from the following components:

| | |
|---|---|
| metalaxyl techn. | 12.0% |
| Cu(I) oxide | 67.6% |
| ligninsulfonate | 6.0% |
| sodium aluminium silicate | ad 100% |

Two webs of polyvinyl alcohol film each having a thickness of 38 µm and a degree of hydrolysis of 95% are fed continuously to a commercial filling machine (available from NEDI S.A., Saint-Mammes, France) in which they are welded by impulse sealing with a main seam to a bag which is sealed at its end with a transverse weld. After being filled with 500 g of metalaxyl wettable powder, each prefabricated bag so obtained is separated by a dividing seam so as to give sealed bags that contain the fungicide concentrate.

Example W2

A gel is prepared from the following components:

| | |
|---|---|
| propiconazole techn. | 62.5% |
| sodium dodecylbenzenesulfonate | 3.0% |
| isotridecyl polyoxyethanol (EO 6) | 3.0% |
| EO-PO block polymer (20% EO; $\overline{MG}$: 5000) | 4.0% |
| silicone oil | 0.2% |
| hydroxypropyl cellulose | 1.0% |
| cyclohexanone | ad 100% | viscosity: 2000 cp

A web of polyvinyl alcohol film obtained by a casting method and having a thickness of 40 µm and a degree of hydrolysis of 86% and a web of polyvinyl alcohol film having a thickness of 38 µm and a degree of hydrolysis of 95% are fed continuously to a commercial filling machine in which they are welded by impulse sealing with a main seam to a bag which is sealed at its end with a transverse weld. After being filled with 100 g of the above propiconazole gel, each prefabricated bag so obtained is separated by a dividing seam so as to give sealed bags that contain the fungicide concentrate. Such heat-sealed bags withstand a drop from a height of 1.2 m at temperatures above 0° C. without damage.

Example W3

A gel is prepared from the following components:

| | |
|---|---|
| propiconazole techn. | 12.5% |
| fenpropidine techn. | 45% |
| mixt. of long-chain fatty alcohols | 2.0% |
| polyethoxylated castor oil with 36 EO units | 12.0% |
| precipitated silicic acid | 3.0% |
| dipropylene glycol methyl ether | ad 100% |

After mixing all liquid components, the silicic acid is dispersed in the mixture by means of high shearing forces (e.g. stirrer with disperser disc) to form a highly viscous homogeneous gel. The viscosity is is c. 6000–8000 cP.

Example W4

A heat-sealed bag is prepared as described in Example W2. The filled weight is 200 g.

Example W5

The gel of Example W3 is filled as described in Example W4 in 250 g portions into heat-sealed bags which consist of 3 layers of a polyvinyl alcohol film each having a thickness of 38 µm and a degree of hydrolysis of 95%.

Example W6

Three webs of polyvinyl alcohol film each having a thickness of 30 µm are fed continuously to a commercial filling machine (available from NEDI S.A., Saint-Mammes, France) in which they are welded by impulse sealing with a main seam to a bag which is sealed at its end with a transverse weld. After being filled with 400 g of propiconazole gel in accordance with Example W2, each prefabricated bag so obtained is separated by a dividing seam so as to give sealed bags that contain the fungicide concentrate.

Example W7

The gel of Example W3 is filled as described in Example W2 in amounts of 500 g into heat-sealed bags that each consist of two layers of polyvinyl alcohol film, the inner film having a thickness of 40 μm and a degree of hydrolysis of 86%, and the outer film having a thickness of 38 μm and a degree of hydrolysis of 95%.

USE EXAMPLES

Example A1

4 heat-sealed bags comprising two layers of polyvinyl alcohol film having a thickness of 38 μm and a degree of hydrolysis of 95% are prepared. Each bag contains 100 g of the gel of Example W2.

60 l of water of 8° C. are charged to a 600 l spray fluid tank. The bags are added, with agitation, and swim on the surface of the water. The first bag opens after 25 seconds and, after 65 seconds, no more intact bags are observed. Stirring is continued for 1 minute and the tank is then bulked to 400 l, stirred for a further 2 minutes, and the mixture is subsequently sprayed from a spray boom through nozzles at a rate of flow of 136–360 l/ha. After application, no residues are found either on the nozzle filters or in the tank.

Example A2

60 l of water of 17° C. are charged to a 600 l spray fluid tank. The 4 bags of Example W5 are then added, with agitation. The first bag opens after 45 seconds and, after 105 seconds, all the bags have opened. The tank is then bulked to 200 l and the mixture is subsequently sprayed as described in Example W7. After application, no residues are found either on the nozzle filters or in the tank.

TEST EXAMPLES

Example T1

Tear Strength of the Two Layer Film

The tear strength of a double layer film of polyvinyl alcohol, each layer having a thickness of 38 μm is measured with a tensile testing apparatus according to DIN 53 455, and compared with that of an analogous laminated film and with monofilms having thicknesses of 38 μm and 82 μm. This is done by preparing film strips with a width of 15 mm and a length of 100 mm and conditioning them for 2 days at 23° C. and 50% relative humidity. These strips are then fixed between retaining clamps at a distance of 40 mm and stretched at a tear rate of 1000 mm/min. What is measured is the force at 5% elongation (F 5%) and on tear (Fm) as well as the maximum elongation (Am.). The following values are measured (average value of 10 repeats in each case):

| Film type | F 5% (N) | Fm (N) | Am (%) | Thickness (μm) |
|---|---|---|---|---|
| monofilm | 2.32 | 32.05 | 492 | 38 |
| monofilm | 3.08 | 43.97 | 550 | 82 |
| laminate film | 4.77 | 55.98 | 510 | 87 |
| double layer film | 3.65 | 60.07 | 509 | 2 × 38 |

The results show that while the mechanical strength of a double layer film matches that of a laminated film of the same thickness, the tear strength of a monofilm of about the same thickness is markedly lower than that of a double layer film.

Example T2

Peel Strength of the Two-layer Film

A film having a thickness of 40 μm and degree of hydrolysis of 86% and a second film having a thickness of 38 μm and a degree of hydrolysis 95% are pressed together flat for several days under a pressure of 18 g/cm². In a comparison test, the same types of film are wetted before being compressed to form a laminate. The force necessary to separate the two films is determined in a tensile testing apparatus. This is done by preparing film strips with a width of 15 mm and a length of 80 mm and conditioning them for 2 days at 23° C. and 50% relative humidity. These strips are then stretched such that the two layers are separated from each other at a tear rate of 50 mm/min. The force necessary to separate the layers of the double layer film is 5.5±0.8 N (average value of 10 repeats). The layers of the laminated film cannot be separated from each other without tearing. To the contrary, the laminated film tears at a force of 5.5±0.8 N.

This comparison shows that the individual layers of a two-layered film stick together loosely only by weak adhesion, whereas the original single layers of the laminated film form a tenacious bond that can no longer be separated mechanically without tearing.

What is claimed is:

1. A sealed container for preserving chemicals which is filled with one or more than one chemical, the container having walls consisting of at least two superimposed single layer homogeneous and water-soluble polymer films that stick together by weak adhesion and are separable without tearing the films.

2. A container according to claim 1, wherein said one or more chemicals are dissolved or dispersed in a liquid or in a gel, or are in the form of water-dispersible powders or granulates.

3. A container according to claim 1, wherein the contents are from 40 to 100% by volume, based on the volume of said container, and the remaining volume is occupied with a gas.

4. A container according to claim 1, wherein the walls consist of natural unmodified or modified polymers or of synthetic polymers.

5. A container according to claim 4, wherein the water-soluble walls consist of polymers containing 50 to 100 mol % of vinyl alcohol units and 0 to 50 mol % of one or more than one comonomer selected from the group consisting of vinyl ether, vinyl acetate, hydroxyalkyl vinyl ether, acrylic acid, methacrylic acid, maleic acid, hydroxyalkyl maleates, acrylates and methacrylates, vinyl pyrrolidone and styrenesulfonic acid.

6. A container according to claim 5, wherein the water-soluble walls consist of polyvinyl alcohol.

7. A container according to claim 1, wherein the container walls are formed of two or three water-soluble polymer films.

8. A container according to claim 1, wherein the overall thickness of each of the container walls is from 20 to 200 μm.

9. A container according to claim 1 having a capacity of 5 to 10000 ml.

10. A container according to claim 1, which has the shape of a sphere, a bag, a tubular bag, a square, a rectangle or a cylinder.

11. A container according to claim 1, wherein at least one polymer film contains a plasticiser.

12. A container according to claim 11, wherein a polymer film containing a plasticiser faces the outside of said container.

13. A container according to claim 1, wherein the chemicals are selected from the group consisting of herbicides, insecticides, pesticides and fungicides, and formulation assistants.

* * * * *